(12) United States Patent
Wu et al.

(10) Patent No.: US 10,704,031 B2
(45) Date of Patent: Jul. 7, 2020

(54) DNA POLYMERASE MUTANTS WITH INCREASED PROCESSIVITY OF DNA SYNTHESIS

(71) Applicants: Jing Wu, Wuxi (CN); Li Wang, Wuxi (CN)

(72) Inventors: Jing Wu, Wuxi (CN); Li Wang, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 0 days.

(21) Appl. No.: 16/198,773

(22) Filed: Nov. 22, 2018

(65) Prior Publication Data

US 2019/0203190 A1    Jul. 4, 2019

Related U.S. Application Data

(63) Continuation of application No. PCT/CN2017/103118, filed on Sep. 25, 2017.

(30) Foreign Application Priority Data

Oct. 26, 2016   (CN) .......................... 2016 1 0945974

(51) Int. Cl.
| | |
|---|---|
| *C12N 9/12* | (2006.01) |
| *C12N 15/52* | (2006.01) |
| *C12N 15/63* | (2006.01) |
| *C12P 19/34* | (2006.01) |

(52) U.S. Cl.
CPC ........... *C12N 9/1252* (2013.01); *C12N 15/52* (2013.01); *C12N 15/63* (2013.01); *C12P 19/34* (2013.01); *C12Y 207/07007* (2013.01)

(58) Field of Classification Search
None
See application file for complete search history.

(56) References Cited

U.S. PATENT DOCUMENTS

| | | | |
|---|---|---|---|
| 9,399,766 B2 * | 7/2016 | Kamtekar | ...... C12Y 207/07007 |
| 2019/0078075 A1 * | 3/2019 | Kokoris | ............... C12N 9/1252 |
| 2019/0203190 A1 * | 7/2019 | Wu | ....................... C12N 9/1252 |

OTHER PUBLICATIONS

PIR Accession No. T46875, published Mar. 17, 2000 (Year: 2000).*
UniProt Accession No. DPO4_SACS2, published Oct. 1, 2001 (Year: 2001).*

* cited by examiner

*Primary Examiner* — Richard C Ekstrom
(74) *Attorney, Agent, or Firm* — Lili Chen

(57) ABSTRACT

Disclosed are Dpo4 DNA polymerase mutants with increased DNA synthesis processivity. The mutant enzymes, Dpo4 A181D and Dpo4 E63K, are constructed based on the wild-type Dpo4 derived from *Sulfolobus solfataricus* to obtain Dpo4DNA polymerase mutants with increased DNA processivity. The extension length of Dpo4 A181D and Dpo4 E63K are respectively increased by 25% and 18.8% than that of the wild-type Dpo4. The fidelity of Dpo4 A181D and wild-type Dpo4 are similar, and the fidelity of Dpo4 E63K is increased from that of the wild-type Dpo4. In summary, the mutants Dpo4 A181D and Dpo4 E63K obtained by the present invention have increased processivity compared to that of the wild-type Dpo4 DNA polymerase.

5 Claims, 6 Drawing Sheets

Specification includes a Sequence Listing.

A

B

SEQUENCE LISTING

<160> NUMBER OF SEQ ID NOS: 9

<210> SEQ ID NO 1
<211> LENGTH: 1059
<212> TYPE: DNA
<213> ORGANISM: Sulfolobus solfataricus

<400> SEQUENCE: 1

```
atgatcgtgc tgttcgtcga cttcgactac ttctacgcgc aggttgaaga agtcctgaac      60
ccgagtctga aaggtaaacc ggttgtcgtt tgcgttttta gcggccgttt cgaagatagc     120
ggtgcagttg caaccgcaaa ttacgaagca cgcaaattcg gcgttaaagc aggtattccg     180
atcgtcgagg cgaaaaagat tctgccgaac gctgtttacc tgccgatgcg caaagaagtt     240
taccagcagg tctcctcccg tattatgaac ctgctgcgcg aatacagcga gaaaatcgaa     300
atcgcgagca ttgacgaagc gtatctggat atcagcgaca agtccgcga  ttatcgcgaa     360 gcgtataacc tgggcctgga gatcaaaaac aaaatcctgg agaaagagaa aatcaccgtc     420
accgtcggca tcagcaaaaa caaagtcttc gcgaaaattg ccgcagatat ggcaaaaccg     480
aacggcatca aagtcatcga cgacgaagag gtcaaacgcc tgattcgcga actggatatc     540
gcggacgttc cgggtattgg taatattacc gcggagaaac tgaaaaaact gggcatcaac     600
aaactggtcg ataccctgag catcgagttc gataaactga aggcatgat  cggcgaggcg     660 aaagcgaaat atctgatcag cctggcacgc gacgaatata cgaaccgat  tcgtacccgc     720 gttcgtaaaa gcattggccg cattgtcacc atgaaacgca cagccgtaa  cctggaagag     780 atcaaaccgt acctgtttcg cgcgattgaa gaaagctact acaaactgga caaacgcatc     840
ccgaaagcga ttcacgttgt tgcagttacc gaggatctgg atattgttag tcgcggtcgt     900
acctttccgc acggtattag caaagagacc gcatatagcg aaagcgtcaa actgctgcag     960
aaaatcctgg aagaagatga acgcaaaatc cgtcgtattg cgtccgctt  tagcaaattc    1020 atcgaggcga tcggcctgga taaattcttc gacacctga                            1059
```

<210> SEQ ID NO 2
<211> LENGTH: 352
<212> TYPE: PRT
<213> ORGANISM: Sulfolobus solfataricus

<400> SEQUENCE: 2

```
Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Cys Val
            20                  25                  30

Phe Ser Gly Arg Phe Glu Asp Ser Gly Ala Val Ala Thr Ala Asn Tyr
        35                  40                  45

Glu Ala Arg Lys Phe Gly Val Lys Ala Gly Ile Pro Ile Val Glu Ala
50                  55                  60

Lys Lys Ile Leu Pro Asn Ala Val Tyr Leu Pro Met Arg Lys Glu Val
65                  70                  75                  80

Tyr Gln Gln Val Ser Ser Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
130                 135                 140

Ser Lys Asn Lys Val Phe Ala Lys Ile Ala Ala Asp Met Ala Lys Pro
145                 150                 155                 160

Asn Gly Ile Lys Val Ile Asp Asp Glu Glu Val Lys Arg Leu Ile Arg
            165                 170                 175

Glu Leu Asp Ile Ala Asp Val Pro Gly Ile Gly Asn Ile Thr Ala Glu
            180                 185                 190

Lys Leu Lys Lys Leu Gly Ile Asn Lys Leu Val Asp Thr Leu Ser Ile
            195                 200                 205

Glu Phe Asp Lys Leu Lys Gly Met Ile Gly Glu Ala Lys Ala Lys Tyr
            210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Ile Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
            275                 280                 285

Val Thr Glu Asp Leu Asp Ile Val Ser Arg Gly Arg Thr Phe Pro His
            290                 295                 300

Gly Ile Ser Lys Glu Thr Ala Tyr Ser Glu Ser Val Lys Leu Leu Gln
305                 310                 315                 320

Lys Ile Leu Glu Glu Asp Glu Arg Lys Ile Arg Arg Ile Gly Val Arg
                325                 330                 335

Phe Ser Lys Phe Ile Glu Ala Ile Gly Leu Asp Lys Phe Phe Asp Thr
            340                 345                 350

<210> SEQ ID NO 3
<211> LENGTH: 15
<212> TYPE: DNA
<213> ORGANISM: Artificial Sequence
<220> FEATURE:
<223> OTHER INFORMATION: Synthetic DNA

<400> SEQUENCE: 3
cgtactcgta ggcat                                                    15
```

-continued

```
<210> SEQ ID NO 4
<211> LENGTH: 50
<212> TYPE: DNA
<213> ORGANISM: Artificial Sequence
<220> FEATURE:
<223> OTHER INFORMATION: Synthetic DNA

<400> SEQUENCE: 4
tcctaccgtg cctacctgaa cagctggtca cactgatgcc tacgagtacg         50

<210> SEQ ID NO 5
<211> LENGTH: 50
<212> TYPE: DNA
<213> ORGANISM: Artificial Sequence
<220> FEATURE:
<223> OTHER INFORMATION: Synthetic DNA

<400> SEQUENCE: 5
tcctaccgtg cctacctgaa cagctggtca cactaatgcc tacgagtacg         50

<210> SEQ ID NO 6
<211> LENGTH: 50
<212> TYPE: DNA
<213> ORGANISM: Artificial Sequence
<220> FEATURE:
<223> OTHER INFORMATION: Synthetic DNA

<400> SEQUENCE: 6
tcctaccgtg cctacctgaa cagctggtca cactcatgcc tacgagtacg         50

<210> SEQ ID NO 7
<211> LENGTH: 50
<212> TYPE: DNA
<213> ORGANISM: Artificial Sequence
<220> FEATURE:
<223> OTHER INFORMATION: Synthetic DNA

<400> SEQUENCE: 7
tcctaccgtg cctacctgaa cagctggtca cacttatgcc tacgagtacg         50

<210> SEQ ID NO 8
<211> LENGTH: 1059
<212> TYPE: DNA
<213> ORGANISM: Artificial Sequence
<220> FEATURE:
<223> OTHER INFORMATION: Synthetic DNA

<400> SEQUENCE: 8
atgatcgtgc tgttcgtcga cttcgactac ttctacgcgc aggttgaaga agtcctgaac         60
ccgagtctga aggtaaaacc ggttgtcgtt tgcgttttta gcggccgttt cgaagatagc        120
ggtgcagttg caaccgcaaa ttacgaagca cgcaaattcg gcgttaaagc aggtattccg        180
atcgtcaagg cgaaaaagat tctgccgaac gctgtttacc tgccgatgcg caaagaagtt        240
taccagcagg tctcctcccg tattatgaac ctgctgcgcg aatacagcga gaaaatcgaa        300
atcgcgagca ttgacgaagc gtatctggat atcagcgaca agtccgcga ttatcgcgaa        360 gcgtataacc tgggcctgga gatcaaaaac aaaatcctgg agaaagaaa atcaccgtc        420 accgtcggca tcagcaaaaa caaagtcttc gcgaaaattg ccgcagatat ggcaaaaccg        480
aacggcatca agtcatcga cgacgaagag gtcaaacgcc tgattcgcga actggatatc        540
gcggacgttc cgggtattgg taatattacc gcggagaaac tgaaaaaact gggcatcaac        600
aaactggtcg ataccctgag catcgagttc gataaactga aaggcatgat cggcgaggcg        660
```

```
aaagcgaaat atctgatcag cctggcacgc gacgaatata acgaaccgat tcgtacccgc    720
gttcgtaaaa gcattggccg cattgtcacc atgaaacgca acagccgtaa cctggaagag    780
atcaaaccgt acctgtttcg cgcgattgaa gaaagctact acaaactgga caaacgcatc    840
ccgaaagcga ttcacgttgt tgcagttacc gaggatctgg atattgttag tcgcggtcgt    900
acctttccgc acggtattag caaagagacc gcatatagcg aaagcgtcaa actgctgcag    960
aaaatcctgg aagaagatga acgcaaaatc cgtcgtattg gcgtccgctt tagcaaattc   1020
atcgaggcga tcggcctgga taaattcttc gacacctga                          1059
```

<210> SEQ ID NO 9
<211> LENGTH: 1059
<212> TYPE: DNA
<213> ORGANISM: Artificial Sequence
<220> FEATURE:
<223> OTHER INFORMATION: Synthetic DNA

<400> SEQUENCE: 9

```
atgatcgtgc tgttcgtcga cttcgactac ttctacgcgc aggttgaaga agtcctgaac     60
ccgagtctga aaggtaaacc ggttgtcgtt tgcgttttta gcggccgttt cgaagatagc    120
ggtgcagttg caaccgcaaa ttacgaagca cgcaaattcg gcgttaaagc aggtattccg    180
atcgtcgagg cgaaaaagat tctgccgaac gctgtttacc tgccgatgcg caaagaagtt    240
taccagcagg tctcctcccg tattatgaac ctgctgcgcg aatacagcga gaaatcgaa     300 atcgcgagca ttgacgaagc gtatctggat atcagcgaca agtccgcga ttatcgcgaa     360 gcgtataacc tgggcctgga gatcaaaaac aaaatcctgg agaaagagaa aatcaccgtc    420
accgtcggca tcagcaaaaa caaagtcttc gcgaaaattg ccgcagatat ggcaaaaccg    480
aacggcatca aagtcatcga cgacgaagag gtcaaacgcc tgattcgcga actggatatc    540
gacgacgttc cgggtattgg taatattacc gcggagaaac tgaaaaaact gggcatcaac    600
aaactggtcg ataccctgag catcgagttc gataaactga aagcatgat cggcgaggcg     660 aaagcgaaat atctgatcag cctggcacgc gacgaatata acgaaccgat tcgtacccgc    720
gttcgtaaaa gcattggccg cattgtcacc atgaaacgca acagccgtaa cctggaagag    780
atcaaaccgt acctgtttcg cgcgattgaa gaaagctact acaaactgga caaacgcatc    840
ccgaaagcga ttcacgttgt tgcagttacc gaggatctgg atattgttag tcgcggtcgt    900
acctttccgc acggtattag caaagagacc gcatatagcg aaagcgtcaa actgctgcag    960
aaaatcctgg aagaagatga acgcaaaatc cgtcgtattg gcgtccgctt tagcaaattc   1020
atcgaggcga tcggcctgga taaattcttc gacacctga                          1059
```

DNA POLYMERASE MUTANTS WITH INCREASED PROCESSIVITY OF DNA SYNTHESIS

CROSS-REFERENCES AND RELATED APPLICATIONS

This application claims priority to, and is a continuation of international application No. PCT/CN2017/103118, entitled "DNA Polymerase Mutants with Increased Processivity of DNA Synthesis", filed Sep. 25, 2017, which claims priority to Chinese application No. 201610945974.6, filed Oct. 26, 2016. The content of both applications are herein incorporated by reference in their entirety.

BACKGROUND OF THE INVENTION

Field of the Invention

The present invention relates to DNA polymerase mutants with increased DNA synthesis extension capacity as compared to that of the wild-type enzyme, which belongs to the field of enzyme engineering.

Description of the Art

The Y-family DNA polymerase Dpo4 is a translesion synthesis polymerase that is capable of replacing the replicative DNA polymerase to cross the template lesion to allow DNA synthesis to continue, which helps the cells resist DNA lesion. However, in order to prevent more mutations, Dpo4 needs to be removed immediately after crossing the lesion and the normal replicative polymerase restores control of DNA synthesis afterwards, which requires that the binding of Dpo4 to DNA is transient. Dpo4 is a typical Y-family DNA polymerase with a typical right-hand structure, which is divided into four domains: a thumb domain, a palm domain, a finger domain, and a little-finger domain. Compared to other DNA polymerases, Dpo4 has a small finger domain, resulting in almost no contact with the major groove of the nascent base pair. Its thumb domain is short and thick, making Dpo4 less effective at binding to DNA and incorporating of nucleosides. Thus Dpo4 imposes few constraints on its DNA substrate. Its structural characteristics and lesser functional requirements of its DNA substrate makes Dpo4 have a low processivity in DNA synthesis.

The essence of processivity is to retain the affinity of the enzyme to the polymeric substrate during multiple rounds of catalysis. Therefore, increasing the affinity of the polymerase to the substrate is the essential way to increase the processivity. In the existing studies, the polymerase processivity was mainly increased by linking corresponding binding proteins, such as the β-slip gripper, thioredoxin, PCNA and the Sso7d protein from *Sulfolobus solfataricus*, to the polymerase. The research on enhancing the affinity of polymerase and DNA by mutating amino acids is mainly reported in the research of reverse transcriptases of some HIV viruses, and there are few studies on mutating Y-family DNA polymerases to enhance their affinity to DNA.

SUMMARY OF THE INVENTION

The present invention aims to provide a Dpo4 DNA-polymerase mutant with increased processivity, which is obtained by mutating amino acid A at the 181st position of the wild-type Dpo4 to D (Dpo4 A181D), or E at the 63rd position to K (Dpo4 E63K) by site-directed mutagenesis.

The processivity refers to the average extension length of the DNA caused by the DNA polymerase binding to the DNA once.

The amino acid A at the 181st position and the amino acid E at the 63rd position are both non-conserved sites.

A nucleotide sequence encoding wild-type Dpo4 is shown in SEQ ID NO:1, and an amino acid sequence of the wild-type Dpo4 is shown in SEQ ID NO:2.

The present invention provides a method for obtaining the Dpo4 DNA polymerase mutants with increased processivity, comprising searching for candidate mutation sites by simulating the binding energy of Dpo4 and DNA by means of molecular dynamics and obtaining the enzyme mutants by site-directed mutagenesis.

The present invention provides mutants of a Dpo4 derived from *Sulfolobus solfataricus* that has increased DNA processivity as compared to the wild-type enzyme. In terms of the processivity, the extension length of the Dpo4 A181D is increased by 25%, and the extension length of the Dpo4 E63K is increased by 18.8% as compared with the wild-type Dpo4. The fidelity of Dpo4 A181D is close to that of Dpo4, and the fidelity of Dpo4 E63K is increased as compared with that of Dpo4. In general, the mutants A181D and E63K obtained by the present invention have increased processivity.

DETAILED DESCRIPTION

The technical details of some embodiments of the present invention are further described and illustrated below with reference to the accompanying drawings in the following examples. The examples are described only for illustration purpose, not to limit the scope of the present invention which is defined by the claims hereafter.

Example 1. Expression and Purification of Dpo4 Protein

Figure 1:
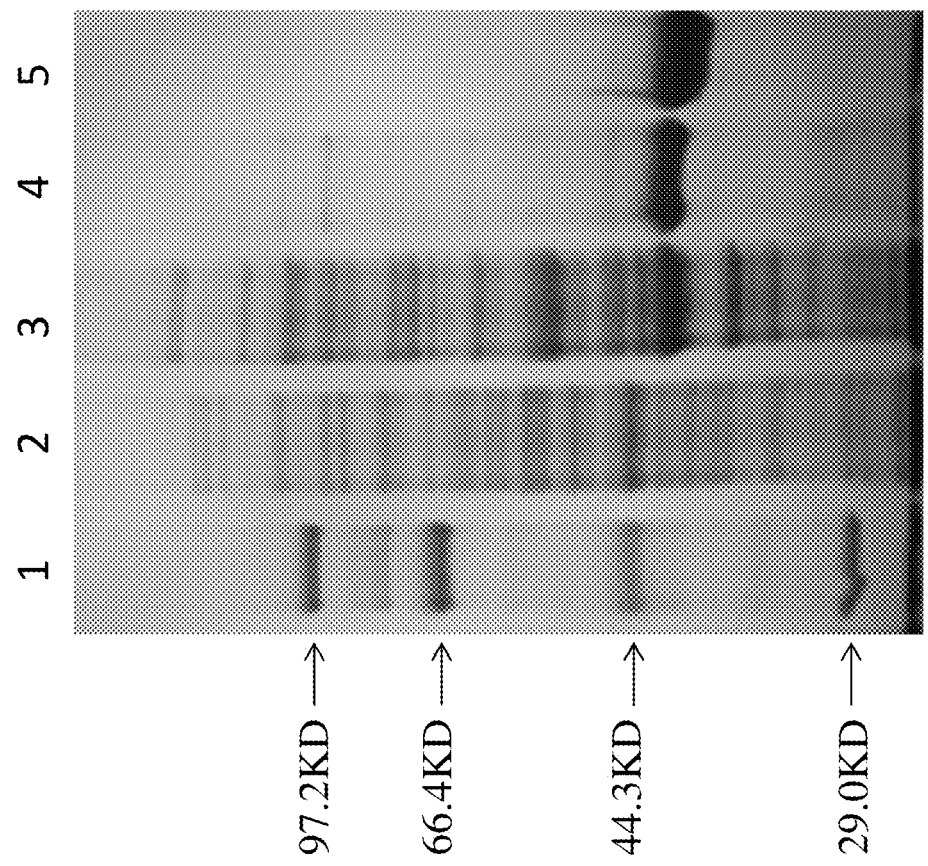
FIG. 1 shows the SDS-PAGE of proteins during steps of expression and purification of Dpo4 protein. Lanes 1, 2, 3, 4, and 5 are the protein marker, uninduced crude enzyme solution, IPTG-induced crude enzyme solution, proteins purified by nickel column from IPTG-induced enzyme solution, and proteins further purified by cation exchange column, respectively.

The Dpo4 target gene with the nucleotide sequence of SEQ ID NO:1 was synthesized by Synbio Technologies (Suzhou, China) and was subjected to enzyme digestion and ligation to construct a recombinant plasmid pET28a-dpo4. The recombinant plasmid pET28a-dpo4 was transformed into an *E. coli* BL21 strain for expression of Dpo4 protein. The pET28a contains a Histidine tag. The expressed protein was first purified through a Ni-NTA gravity column, and then purified through a cation exchange column Mono-S until only single protein band is detectable. The purity of the target protein was determined by SDS-PAGE. The purified Dpo4 protein was stored at −80° C. in a 50 mM Tris-HCl buffer containing 50 mM NaCl, 1 mM dithiothreitol and 50% glycerol (v/v) (pH 7.7 when measured at 22° C.). The results of expression and purification of protein are shown in FIG. 1. It was shown from the lanes 2 and 3 that *E. coli* BL21 expressed Dpo4 only after ITPG induction and did not have background expression. As shown in lane 5, after two steps of purification, only a single band of the target protein is detectable in the SDS-PAGE.

Example 2. Determination of Dpo4 Mutation Sites

By homologous sequence comparison, the non-conserved sites in the Dpo4 sequence and the mutation direction and frequency of these sites were determined. The results are shown in Table 1. Ten mutation directions of F33Y, F37T, I59M, E63K, M76I, A181D, N188S, A220S, I248Y, and V289I were determined, and the binding of the ten Dpo4 mutants to DNA and the binding free energy were simulated by the computer. The results are shown in Table 2. Theoretically, the decrease in binding free energy leads to more stable binding between the enzyme and the substrate, resulting in the higher affinity between the enzyme and the substrate and thus increased processivity of the enzyme. It can be seen from the analysis of Table 2 that all mutations except F37T and A220S can increase the processivity of the enzyme.

TABLE 1

Types of mutated residues and frequency of mutation in non-conserved amino acids

| Mutation Location | Primary Amino Acid | Mutated Residues/Frequency of Mutation |
|---|---|---|
| 33 | F | Y/23 |
| 36 | R | K/1 |
| 37 | F | T/21、G/2、N/4、S/3 |
| 38 | E | K/18、S/1、Q/1、G/1、A/1 |
| 39 | D | T/10、N/4、K/3、R/1、H/1、S/1 |
| 40 | S | R/2 |
| 42 | A | V/2、S/1 |
| 43 | V | I/7 |
| 44 | A | S/2 |
| 57 | A | S/14 |

TABLE 1-continued

Types of mutated residues and frequency of mutation in non-conserved amino acids

| Mutation Location | Primary Amino Acid | Mutated Residues/Frequency of Mutation |
|---|---|---|
| 58 | G | A/1 |
| 59 | I | M/29、L/2 |
| 60 | P | A/3、S/1 |
| 61 | I | L/5、T/1、C/1 |
| 62 | V | P/8、I/12、S/4、K/4、Y/1、Q/1、A/1 |
| 63 | E | K/20、R/5、Q/5、A/1、F/1、T/1、S/1 |
| 76 | M | I/9、V/2、A/3、P/1 |
| 78 | K | L/1、R/1、H/1、F/2 |
| 103 | S | G/2 |
| 156 | D | E/9、S/2、G/2 |
| 181 | A | D/14、G/4、E/3、S/8、N/2、K/4 |
| 183 | V | I/19、L/4、F/1 |
| 184 | P | H/2、Y/1、W/1 |
| 186 | I | V/19 |
| 188 | N | S/11、K/9、D/6、E/3 |
| 189 | I | E/3 |
| 190 | T | T/1、A/1、R/1、 |
| 217 | I | P/1 |
| 219 | E | V/18、S/4、K/6、M/1、L/15、I/8、Q/1、V/6、T/7、L/4、F/5、K/17、R/3、N/3、P/1、Q/1、T/1 |
| 220 | A | S/10、K/4、N/1 |
| 221 | K | R/5、F/1 |
| 240 | R | K/12 |
| 241 | V | S/5、T/1、E/8、N/1、Q/2、P/2、I/4、K/1 |
| 242 | R | K/8、V/3、I/2、P/1、A/1、S/1 |
| 243 | K | I/4、V/3、T/1、H/1、S/2、Q/1、D/1、E/1 |
| 244 | S | P/8、H/8、N/5、Q/4 |
| 245 | I | H/9、Q/1、K/1、R/3、M/1、F/3、Y/3、L/1 |
| 246 | G | S/2 |
| 247 | R | K/2 |
| 248 | I | Y/22、E/1 |
| 249 | V | L/13、I/3、M/1、A/2、T/1 |
| 271 | E | D/4、S/4、A/1、Q/1、K/1 |
| 275 | K | R/1、Q/1 |
| 285 | H | T/11、Y/6、A/4、S/7、G/1、V/1 |
| 289 | V | I/28、K/1 |
| 293 | L | I/1、F/1、A/1 |
| 294 | D | N/3、S/1、E/2、T/1、K/1 |
| 295 | I | T/3、Y/1 |
| 296 | V | L/7、I/3、Y/1、Q/1 |
| 297 | S | T/4、Q/1 |
| 298 | R | K/13、H/1 |
| 299 | G | S/11、E/4、Q/1、N/1 |
| 301 | T | K/7、S/6、D/1、Q/1 |
| 321 | K | E/10、Q/4、D/1、R/1、N/1、T/1 |
| 325 | E | R/6、K/4、S/6、A/3 |
| 332 | R | Q/1、P/1、T/1 |
| 336 | R | L/1 |
| 339 | K | K/6、T/1、N/11、D/1、G/2、Q/1 |

TABLE 2

Binding free energy of Dpo4 and mutants to DNA complexes

| Mutant | DNA Complexes P(5'-3')/ T(3'-5') | Binding Free Energy $\Delta G_{bind}$ (kcal/mol) | $(\Delta G_{bind})^{Mutant} - (\Delta G_{bind})^{wt}$ (kcal/mol) | |
|---|---|---|---|---|
| wtDpo4 | P | −1619.7 | 0 | 0 |
| | T | −2346.7 | 0 | |
| F33Y | P | −1721.8 | −102.1 | −100.2 |
| | T | −2344.8 | 1.9 | |
| F37T | P | −1619.3 | 0.4 | 3.5 |
| | T | −2343.6 | 3.1 | |
| I59M | P | −1713.8 | −94.1 | −209.1 |
| | T | −2461.5 | −115.0 | |
| E63K | P | −1621.2 | −1.5 | −152.7 |
| | T | −2497.9 | −151.2 | |
| M76I | P | −1615.4 | 4.3 | −88.7 |
| | T | −2439.7 | −93 | |
| A181D | P | −1572.6 | 47.1 | −105.1 |
| | T | −2498.9 | −152.2 | |
| N188S | P | −1592.7 | 27 | −63.8 |
| | T | −2437.5 | −90.8 | |
| A220S | P | −1566.2 | 53.5 | 33.7 |
| | T | −2366.5 | −19.8 | |
| I248Y | P | −1649.0 | −29.3 | −209.6 |
| | T | −2527.0 | −180.3 | |
| V289I | P | −1628.9 | −9.2 | −161.5 |
| | T | −2499.0 | −152.3 | |

Example 3. Construction of Dpo4 Mutant Enzymes and Comparison of the Processivity of Dpo4 Enzymes Ten mutants Dpo4 F33Y, Dpo4 F37T, Dpo4 I59M, Dpo4 E63K, Dpo4 M76I, Dpo4 A181D, Dpo4 N188S, Dpo4 A220S, Dpo4 I248Y and Dpo4 V289I were respectively constructed by site-directed mutagenesis. The nucleotide sequence encoding the wild-type Dpo4 is as shown in SEQ ID NO:1, and the amino acid sequence of the wild-type Dpo4 is as shown in SEQ ID NO:2.

Figure 2:
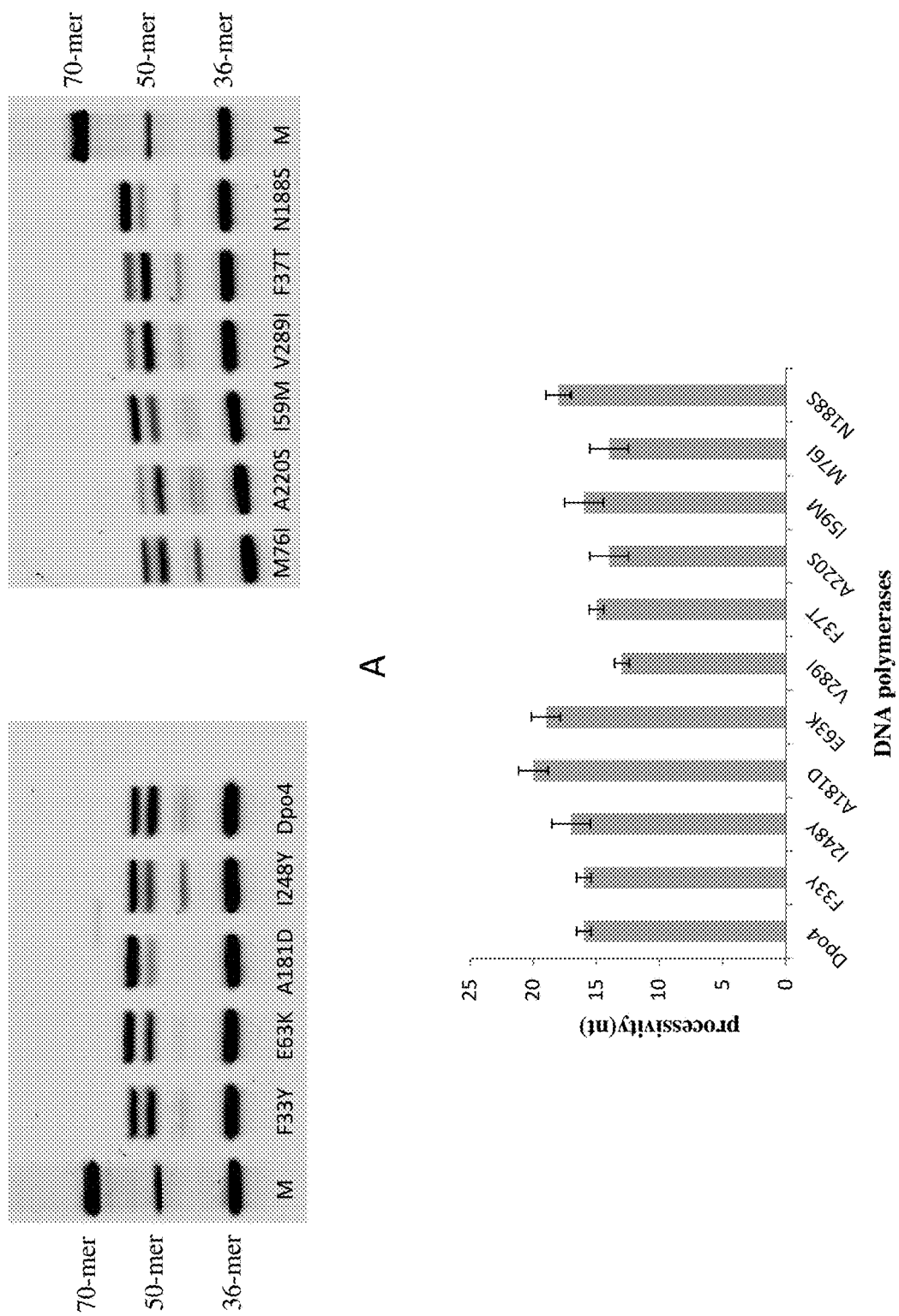
FIG. 2 shows the comparison of the processivity of Dpo4 wild-type enzyme and mutant enzymes. (A), The products made by primer extension using wild-type Dpo4 and mutant enzymes were separated by SDS-PAGE. M, molecular mass markers. (B), The processivity value of each enzyme was calculated by a method taking into consideration of both the length and the intensity of the three main bands in the primer extension experiment.

The processivity of Dpo4 and ten mutant enzymes was evaluated by primer extension assays. A constant concentration (10 nM) of annealed fluorescently labeled primer/template was added to a reaction buffer (10 mM HEPES NaOH (pH 7.4), 50 mM NaCl, 10 mM $MgCl_2$, 200 mM dNTPs, 1 mM DTT, 100 μg/ml BSA, and 0.1% Triton X-100). 100 nM Dpo4 or mutant enzymes was added to initiate DNA synthesis at 37° C., and a 50-mer single-stranded sequence 5000 times more than the substrate was used as a Trap to ensure that the enzyme is bound to DNA only once. After incubation for 5 min, 10 μL of stop solution (80% formamide, 1 mg/mL xylene C, 1 mg/mL bromophenol blue, 20 mM EDTA) was added for quenching the primer extension reaction. The reaction product was denatured at 95° C. for 5 minutes, and placed on ice for 10 min. The reaction mixture was separated on 20% Urea-PAGE and the gel was scanned by Typhoon Trio. The results are shown in FIG. 2.

The processivity of a DNA polymerase is defined as the average extension band length under the condition that the DNA polymerase is allowed to bind to the DNA template only once. As shown in FIG. 2A, the content of the main bands of Dpo4 and the mutant enzyme-directed extensions were significantly different. Based on relative fluorescence of each band of the extension products of Dpo4 or the mutant enzymes, the average extension length was calculated as weighted average length of all the extension bands for each enzyme, and used as a measure of the processivity for that enzyme.

Using this method, the processivity of the wild-type Dpo4 is found to be 16 nt. In the existing literature, the extension length of wild-type Dpo4 was reported to be about 50-100 nt when the enzyme was 20 times more than DNA and the extension assay was performed in the absence of Trap sequences. The higher number reported is likely because of the usage of higher amount of enzyme and multiple times of bindings between the enzyme and the DNA due to lack of Trap sequences. Under the present condition, when the Trap sequences are added and Dpo4 is only 10 times more than the DNA template, the processivity of Dpo4 is measured to be 16 nt.

The average extended band length of all mutants was calculated according to the same method used for the wild-type Dpo4 (FIG. 2B). As compared with the wild-type Dpo4, the extension length of Dpo4A181D and Dpo4E63K was increased by 25% and 18.75%, respectively. The extension length of Dpo4 V289I, Dpo4 A220S, Dpo4 M76I and Dpo4 F37T was decreased, wherein the Dpo4 V289I has the most significant decrease of 18.75% as compared to that of the wild-type Dpo4. The rest of the Dpo4 mutants have similar processivity to that of the wild-type Dpo4. The results of the processivity of the mutants indicated that the mutants with increased binding energy could increase the processivity of Dpo4, and the mutants with decreased binding energy exhibited lower processivity than that of the wild-type Dpo4.

In summary, the processivity of Dpo4E63K, Dpo4N118S, Dpo4A181D and Dpo4I248Y is increased while the processivity of Dpo4F37T, I59M, Dpo4M76I, Dpo4A220S and Dpo4V289I is decreased, and the Dpo4F33Y and Sdbh I62V mutations had no effect on the processivity, indicating that molecular dynamics simulation methods can play a predictive role to a certain extent.

Example 4. Comparison of the Fidelity of Dpo4 and the Mutant Enzymes

The Dpo4 A181D and Dpo4 E63K with a significant increase in processivity and Dpo4 V289I with the most significant decrease in processivity were compared with the wild-type Dpo4 in terms of the fidelity in the presence of $Mn^{2+}$. The primer extensions of the four templates, $T_A$, $T_T$, $T_G$ and $T_C$ (see Table 3), were performed with either a single base (dATP, dCTP, dGTP or dTTP) or a four-base mixture (dNTPs). A 20 nM annealed primer/template was added to a reaction buffer (10 mM HEPES NaOH (pH 7.4), 50 mM NaCl, 10 mM $MgCl_2$, 200 mM dNTPs, 1 mM DTT, 100 μg/ml BSA, and 0.1% Triton X-100). 10 nM DNA polymerase was added to initiate DNA synthesis at 37° C. After incubation for 2 hr, 10 μL of stop solution was added to quench the reaction. The reaction product was separated by 20% Urea-PAGE, and the gel was quantitated using a Typhoon 9400 scanner and ImageQuant software (GE Healthcare, USA).

Figure 3A:
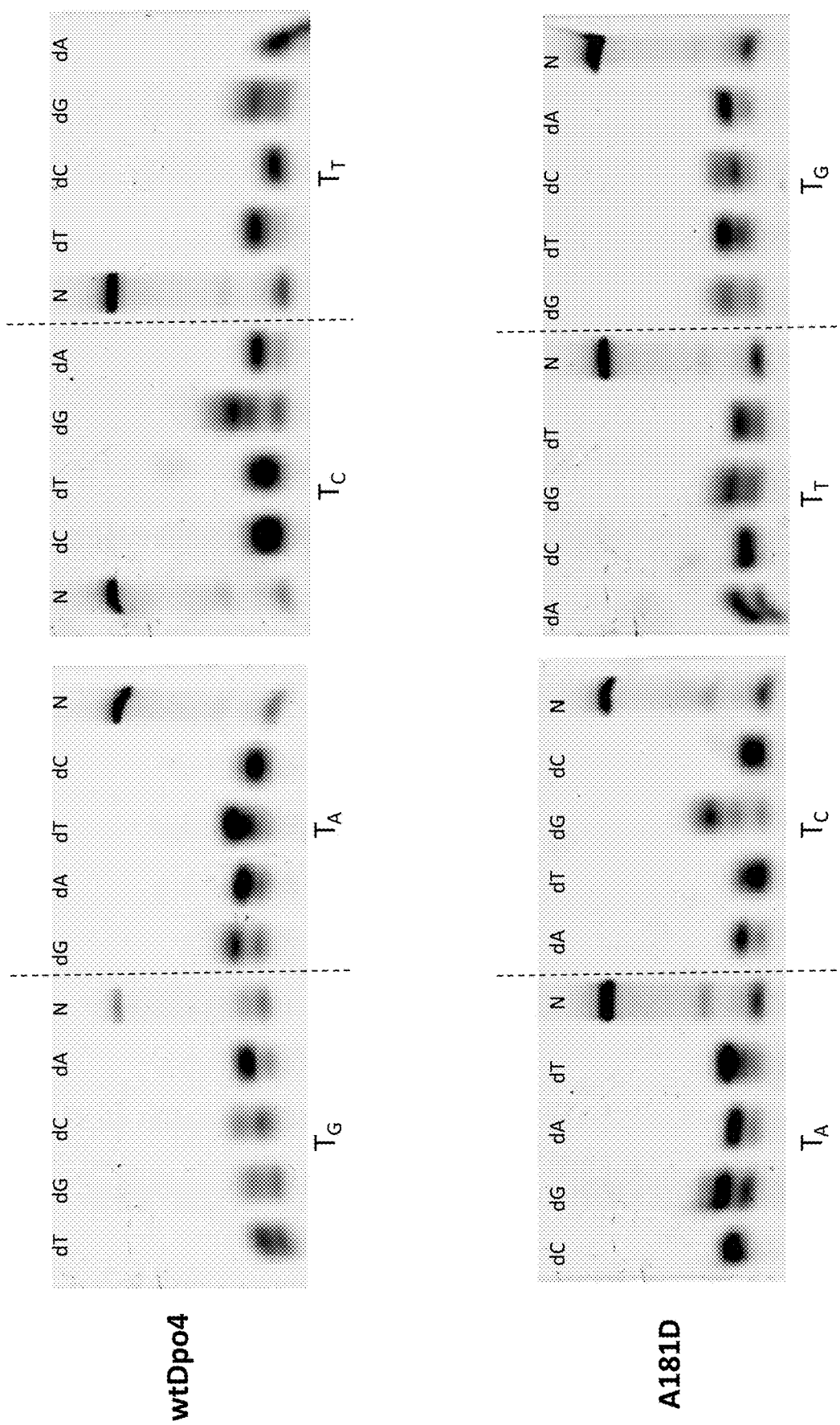
FIG. 3A-3C shows the comparison of fidelity of wild-type Dpo4 and mutant enzymes. (3A), The results for primer extension assay are displayed, wherein wtDpo4 or A181D mutant was incubated with four different DNA templates ($T_A$, $T_T$, $T_C$ or $T_G$) in the presence of a single dNTP (e.g. dA, dT, dC or dG) or a mixture of four dNTPs (labeled as "N"). The sequences of templates $T_A$, $T_T$, $T_C$ and $T_G$ are shown in Table 3. (3B) The results for primer extension assay are displayed, wherein E63K or I248Y mutant was incubated with four different DNA templates ($T_A$, $T_T$, $T_C$ or $T_G$) in the presence of a single dNTP or a mixture of four dNTPs. (3C), 3D plot showing the misincorporation profile of wtDpo4 and the mutants. The percentage of misincorporation of the respective nucleotide is plotted on the z-axis. Four different template DNAs $T_A$, $T_T$, $T_C$ and $T_G$ are represented on the y-axis. The single nucleotide (dATP, dTTP, dGTP or dCTP) added during the extension assay is shown on the x-axis, and the four polymerases, wtDpo4, A181D, E63K and I248Y mutants, are also shown on the x-axis.
Figure 3B:
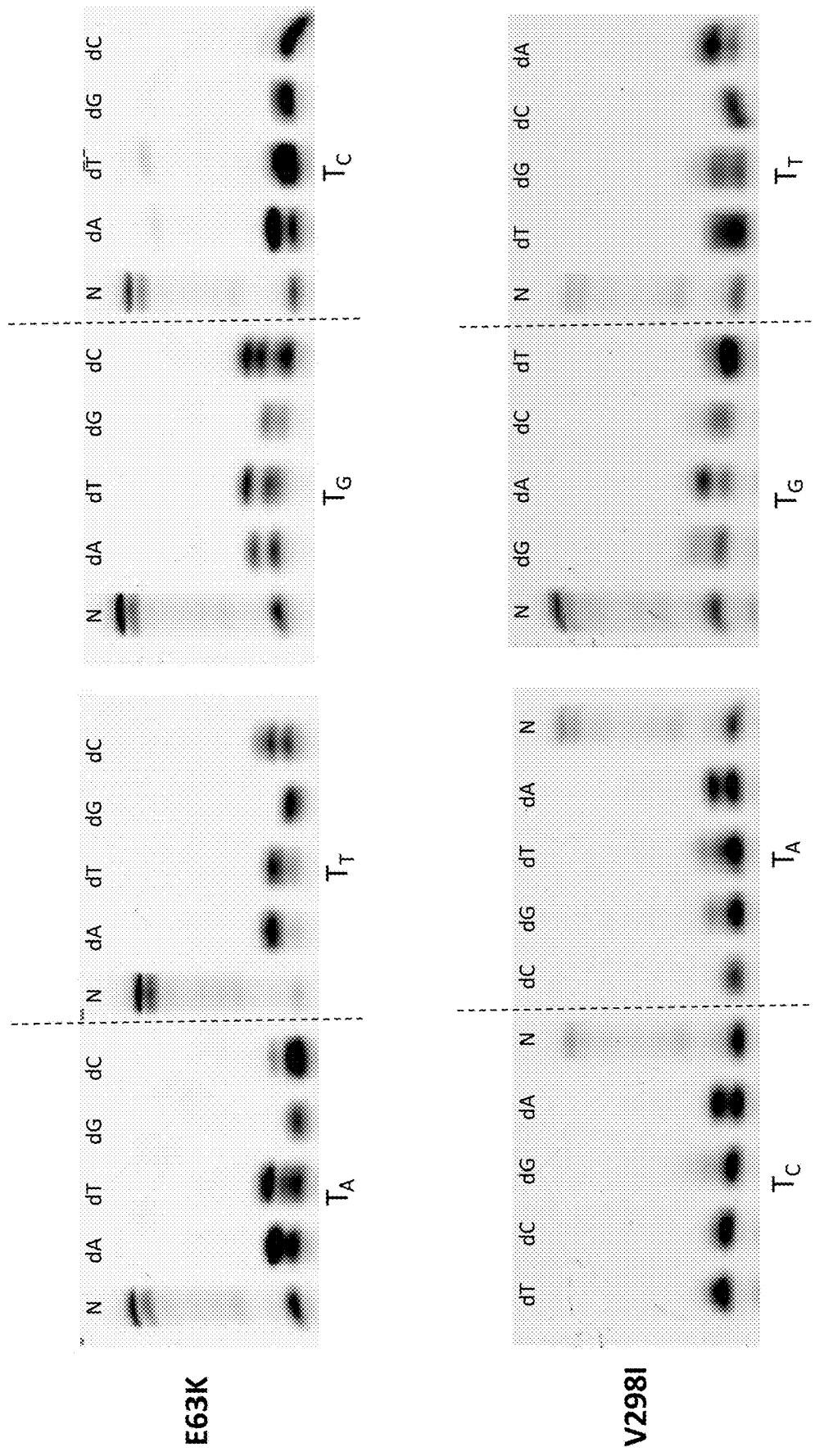
Figure 3C:
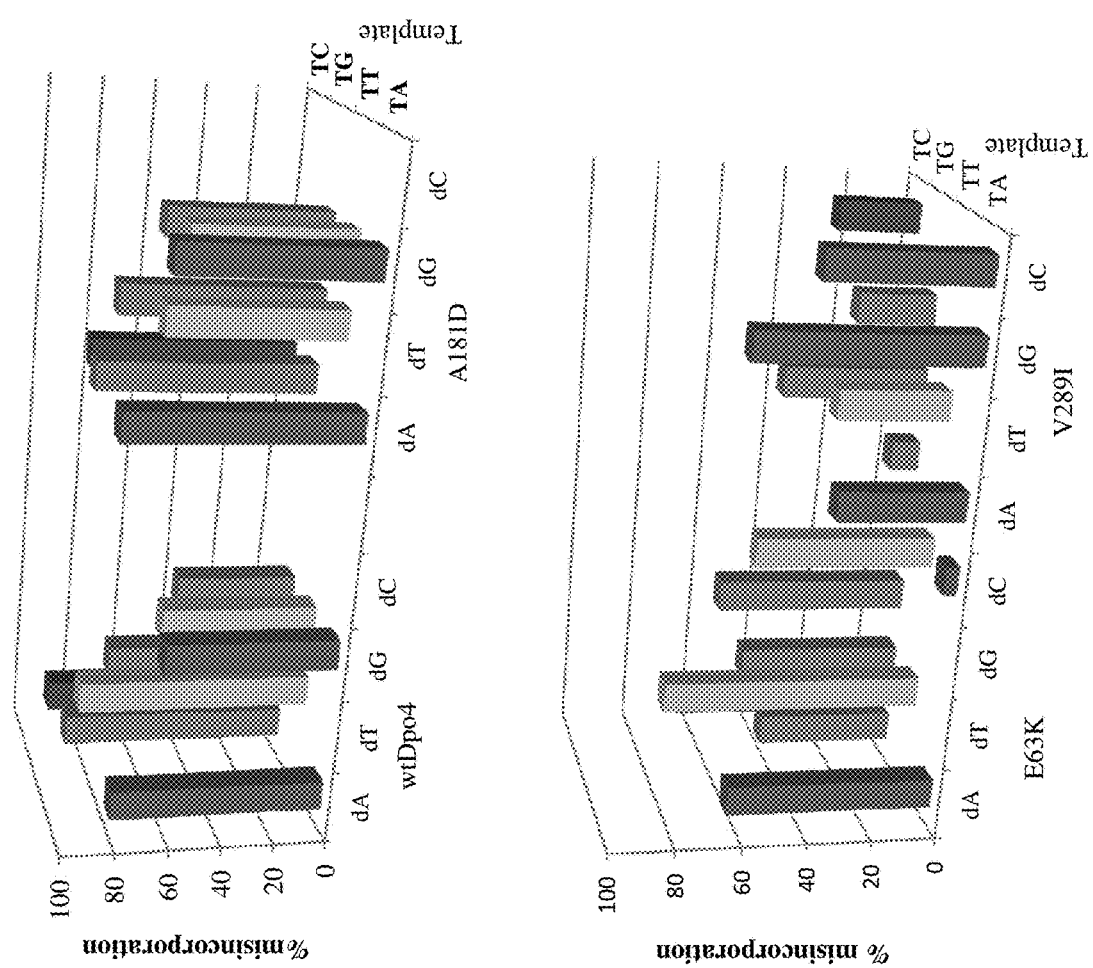

The results are as shown in FIG. 3. Correct nucleotides were well incorporated by Dpo4 and mutants for all of the four templates (see FIG. 3A-3B). However, there was a significant difference among Dpo4 and mutant enzymes in the terms of mismatched nucleotide incorporation. The ratio of mismatched incorporation is higher for wtDpo4 and A181D than for E63K and V289I. From the statistical analysis of mismatched cases (FIG. 3C), Dpo4 and A181D had significantly more types and amount of mismatched extensions than that of E63K and V289I. The fidelity of A181D and wtDpo4 is quite similar under tested condition with $Mn^{2+}$.

The incorporation rate is calculated as follows. A Cy3-labeled 15-mer primer was annealed to a 50-mer DNA template and was subjected to be extended by wtDpo4 or one of its mutant enzymes in the presence of a single nucleotide or a mixture of the four nucleotides. If there are extended products, more than one fluorescent bands can detected; if no extension occurs, only the primer band can be detected. The extension reaction products were separated by a 20% Urea-PAGE, and the gel was quantitated using a Typhoon 9400 scanner and ImageQuant software. Nucleotide incorporation was calculated using the following equation:

$$\% \text{ incorporation} = \frac{I_s}{(I_s + I_p)} \times 100$$

where $I_s$=intensity of the extension band and $I_p$=intensity of the primer band in the same lane.

When using $T_A$ as the template, the incorporation rate of nucleotide dATP was about 80%. When using $T_T$ as the template, the incorporation rate of dTTP for Dpo4 was 88.4%, while that of Dpo4A181D was only 67.4%. However, when using $T_G$ as the template, A181D has more mismatches than that of Dpo4. The incorporation rates of dATP, dTTP and dGTP for A181D were respectively 73.2%, 60.9%, and 63.1%, while the incorporation rates for Dpo4 were only 64.9%, 59.5% and 46.7%, respectively.

Therefore, the mis-incorporation rate of A181D was higher than that of Dpo4, and its fidelity was lower than that of Dpo4. The mis-incorporation rate of dTTP for Dpo4 E63K reached 80% only when the template was $T_T$, and the mis-incorporation rate was lower than 60% under all other mismatched conditions. The mis-incorporation rate of V289I was 67.58% when dGTP was incorporated into the template $T_A$, which was the maximum mis-incorporation rate for V289I.

Based on the statistical analysis of mismatched cases, the fidelity of A181D and wtDpo4 are similar. The fidelity of E63K is higher than that of Dpo4 and Dpo4A181D, and mutant V289I has the least mismatches and the highest fidelity. The order of fidelity from high to low is: V289I, E63K, Dpo4, and A181D, suggesting that the increase of the processivity is not necessarily related to the change of fidelity.

TABLE 3

Primers and template sequences used in fidelity experiments

| Template/Primer | Sequence (5'-3') |
|---|---|
| Primer | 5'-Cy3-CGTACTCGTAGGCAT-3' (SEQ ID NO: 3) |
| $T_G$ | 5'-TCCTACCGTGCCTACCTGAACAGCTGGTCACACTGATGCC TACGAGTACG -3' (SEQ ID NO:4) |
| $T_A$ | 5'-TCCTACCGTGCCTACCTGAACAGCTGGTCACACTAATGCC TACGAGTACG -3' (SEQ ID NO: 5) |
| $T_C$ | 5'-TCCTACCGTGCCTACCTGAACAGCTGGTCACACTCATGCC TACGAGTACG -3' (SEQ ID NO: 6) |

TABLE 3-continued

Primers and template sequences used in fidelity experiments

| Template/Primer | Sequence (5'-3') |
|---|---|
| $T_T$ | 5'-TCCTACCGTGCCTACCTGAACAGCTGGTCACACTTATGCC TACGAGTACG -3' (SEQ ID NO: 7) |

Example 5. Comparison of Nucleotide Incorporation Efficiency of Dpo4 and Mutant Enzymes To compare the nucleotide incorporation efficiency of Dpo4 and mutant proteins is to compare the difference in pre-steady-state kinetics of nucleotide incorporation among Dpo4 and mutant proteins. A 30 nM (50-mer/15-mer) primer extension reaction was initiated with addition of 120 nM Dpo4 or mutant proteins. After different periods of time, the DNA polymerization was terminated by EDTA. The product was separated in a 20% polyacrylamide gel, and the concentration of the extension products was obtained by Typhoon quantitative analysis. The reaction rate constant ($K_{obs}$) under a specific dNTP concentration was calculated according to the formula $[\text{product}]=A(1-\exp(-K_{obs}t))$.

Figure 4:
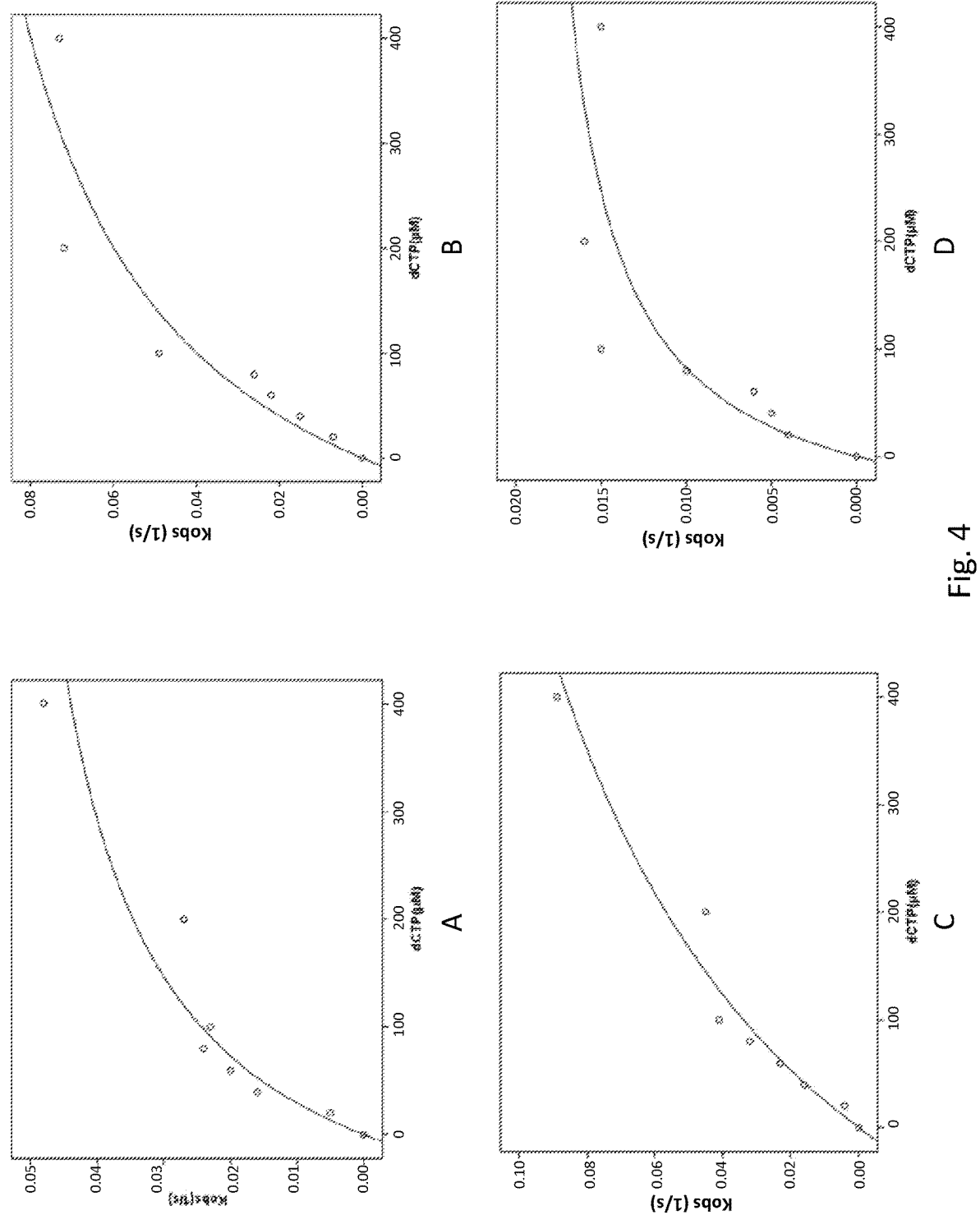
FIG. 4 shows comparison of nucleotide incorporation efficiency of Dpo4 wild-type enzyme and mutants. (A), wtDpo4; (B), A181D; (C), E63K; and (D), I248Y.

By varying the concentration (20-400 μM) of dNTP, the SPSS non-linear fitting equation of $K_{obs}$ and dNTP (FIG. 4) $K_{obs}=K_p[\text{dNTP}]/\{[\text{dNTP}]+K_{d,dNTP}\}$ was used to calculate the maximum nucleotide incorporation rate $K_p$ and the equilibrium dissociation constant $K_{d,dNTP}$, thereby calculating the corresponding nucleotide incorporation efficiency ($K_p/K_{d,\,dNTP}$).

As can be seen from Table 4, the nucleotide incorporation rates ($K_p$) of A181D and E63K are respectively 1.8 and 2.6 times that of wtDpo4, and $K_{d,dNTP}$ of A181D and E63K are respectively 1.7 and 3 times that of wtDpo4. As a result, there is little difference in terms of nucleotide incorporation efficiency for these three enzymes. The nucleotide incorporation efficiency of Dpo4V289I is 45.9% lower than that of the wild-type Dpo4. This lower nucleotide incorporation efficiency may explain why V289I has better fidelity than wtDpo4 and other mutants. $K_{d,dNTP}$ reflects the binding affinity of the ground state for correct nucleotide incorporation, indicating the strength of interaction of Dpo4 and adjacent base pairs.

According to the results, the $K_{d,dNTP}$ of the two mutants A181D and E63K with increased processivity had weaker binding affinity than that of the wtDpo4, possibly because the increase of the processivity of the mutants requires the enzyme-DNA-dNTP complex to switch from the "open state" to the "closed state" faster. This process requires a conformational change in the finger and LF regions of Dpo4, which attenuates the interaction between dNTP and Dpo4, making the interaction between Dpo4 and the duplicated base pair more loose, resulting in an increase in $K_{d,dNTP}$ value. The lower processivity of Dpo4V289I, on the other hand, corresponds to stronger ground state affinity of the enzyme and DNA and dNTP.

In summary, the nucleotide incorporation efficiency of the two mutants A181D and E63K was similar to that of Dpo4 while the nucleotide incorporation efficiency of Dpo4V289I was greatly reduced. A181D and E63K had no effect on the nucleotide incorporation efficiency while the two mutants have increased the processivity.

TABLE 4

Analysis of nucleotide incorporation
efficiency of Dpo4 and mutant enzymes

| Mutant | Maximum Reaction Rate ($S^{-1}$) | Equilibrium Dissociation Constant (μM) | Nucleotide Incorporation Efficiency ($S^{-1} \mu M^{-1}$) |
| --- | --- | --- | --- |
| Dpo4 | 0.066 ± 0.009 | 142.38 ± 18.36 | $4.64 \times 10^{-4}$ |
| Dpo4A181D | 0.12 ± 0.004 | 243.09 ± 41.19 | $4.94 \times 10^{-4}$ |
| Dpo4E63K | 0.177 ± 0.003 | 432.52 ± 10.76 | $4.09 \times 10^{-4}$ |
| Dpo4V289I | 0.021 ± 0.004 | 83.65 ± 5.81 | $2.51 \times 10^{-4}$ |

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A Dpo4 DNA polymerase mutant with increased processivity as compared to its wild-type counterpart enzyme, wherein the wild-type enzyme is Dpo4 DNA polymerase having the amino acid sequence of SEQ ID NO: 2, and wherein the Dpo4 DNA polymerase mutant has a single-point mutation with mutating Alanine at the 181st position of the wild-type Dpo4 DNA polymerase to Aspartic acid, or Glutamic acid at the 63rd position to Lysine.

2. A method for obtaining the Dpo4 DNA polymerase mutant of claim 1, comprising mutating Alanine at the 181st position of the wild-type Dpo4 DNA polymerase to Aspartic acid, or Glutamic acid at the 63rd position to Lysine by site-directed mutagenesis.

3. A gene encoding the DNA polymerase mutant of claim 1, comprising the nucleic acid sequence SEQ ID NO:8 or SEQ ID NO:9.

4. A vector or recombinant cell that comprises the gene of claim 3.

5. A kit containing the Dpo4 DNA polymerase mutant of claim 1.

* * * * *